United States Patent
Mertsching et al.

(10) Patent No.: US 8,279,434 B2
(45) Date of Patent: Oct. 2, 2012

(54) ARRANGEMENT AND METHOD FOR ANALYSIS OF BIOLOGICAL SAMPLES

(75) Inventors: Heike Mertsching, Sindelfingen (DE); Gerd Sulz, Ehrenkirchen (DE); Hagen Thielecke, Blieskastel (DE); Carsten Bolwien, Freiburg (DE); Steffen Koch, Stuttgart (DE)

(73) Assignees: Fraunhofer-Gesellschaft zur Förderung der angwandten Forschung, e.V., München (DE); Universität Stuttgart, Stuttgart (DE)

( * ) Notice: Subject to any disclaimer, the term of this patent is extended or adjusted under 35 U.S.C. 154(b) by 478 days.

(21) Appl. No.: 12/514,792

(22) PCT Filed: Nov. 9, 2007

(86) PCT No.: PCT/EP2007/009736
§ 371 (c)(1),
(2), (4) Date: May 13, 2009

(87) PCT Pub. No.: WO2008/058683
PCT Pub. Date: May 22, 2008

(65) Prior Publication Data
US 2010/0315628 A1      Dec. 16, 2010

(30) Foreign Application Priority Data
Nov. 14, 2006   (DE) .......................... 10 2006 053 540

(51) Int. Cl.
*G01J 3/44* (2006.01)
(52) U.S. Cl. ...................................... 356/301
(58) Field of Classification Search .................. 356/301, 356/72–73
See application file for complete search history.

(56) References Cited

U.S. PATENT DOCUMENTS

| | | |
|---|---|---|
| 5,112,745 A | 5/1992 | Lorr |
| 5,424,959 A | 6/1995 | Reyes et al. |
| 5,442,438 A | 8/1995 | Batchelder et al. |
| 5,866,430 A | 2/1999 | Grow |
| 2002/0022246 A1* | 2/2002 | Lin et al. .................. 435/31 |
| 2002/0074513 A1* | 6/2002 | Abel et al. ............... 250/458.1 |
| 2004/0155202 A1* | 8/2004 | Poteet et al. ............. 250/461.1 |
| 2006/0170916 A1* | 8/2006 | Voigt et al. .............. 356/301 |
| 2007/0155469 A1* | 7/2007 | Johnson .................. 463/17 |
| 2007/0279629 A1* | 12/2007 | Grun et al. .............. 356/318 |

FOREIGN PATENT DOCUMENTS

| WO | WO 91/05238 | 4/1991 |
|---|---|---|
| WO | WO 2004/099763 | 11/2004 |
| WO | WO 2006/091223 | 8/2006 |

OTHER PUBLICATIONS

English translation of the International Preliminary Report on Patentability, Mar. 3, 2009.

(Continued)

*Primary Examiner* — Tarifur Chowdhury
*Assistant Examiner* — Abdullahi Nur
(74) *Attorney, Agent, or Firm* — Bateman IP (57) ABSTRACT

The invention lies in the technical field of cell biology and transplantation medicine. It concerns devices and methods for rapid and noninvasive analysis or checking of biological samples, especially for sterility control, for characterization of infectious particles and microorganisms contained in the biological sample and for characterization of tissue cells and transplants. The main areas of application of the invention are biotechnological production of pharmacological active ingredients and therapeutic agents as well as transplantation medicine.

39 Claims, 1 Drawing Sheet

OTHER PUBLICATIONS

Maquelin et al., Prospective Study of the Performance of Vibrational Spectroscopies for Rapid Identification of Bacterial . . . , Journal of Clinical Micro., Jan. 2003, p. 324-329, vol. 41, No. 1.

Naumann, Infrared and NIR Raman Spectroscopy in Medical Microbiology, Published Before Aug. 16, 2004.

International Search Report for PCT/EP2007/009736, Jul. 2, 2008.
International Preliminary Examination Report for PCT/EP2007/009736, Mar. 3, 2009.

* cited by examiner

ARRANGEMENT AND METHOD FOR ANALYSIS OF BIOLOGICAL SAMPLES

BACKGROUND OF THE INVENTION

1. The Field of the Invention

The present invention lies in the technical field of cell biology and transplantation medicine. It concerns devices and methods for rapid and noninvasive analysis or checking of biological samples, especially for sterility control, for characterization of infectious particles and microorganisms contained in the biological sample and for characterization of tissue cells and transplants. The main areas of application of the invention are biotechnological production of pharmacologically active ingredients and therapeutic agents as well as transplantation medicine.

2. The Relevant Technology

The first aspect of the invention concerns contamination and quality control especially in transplantation medicine. In individual therapy of organ defects with organ-like tissue cultures, for example, skin or cartilage transplants, freedom from germs of the biological implants is a legally prescribed condition for release for implantation. The detection of contaminating microorganisms like bacteria and fungi is only possible with a time delay in the known detection methods. Sterility and contamination checks of biological implants have thus far occurred via known contact and smear samples of the fluids being investigated in subsequent incubation. A shortcoming is that the results of analysis with characterization of the contaminating microorganism, which is sometimes only a slowly growing pathogen, is only available about 2 weeks after release of the biological implant for implantation in the patient. Only then can corresponding therapeutic steps against the detected contamination be initiated, for example, specific antibiotic therapy. Means and methods are therefore desirable through which contamination of biological implants could be sensitively and selectively detected within a short time, and the existing contaminated microorganism characterized and, if necessary, identified.

For quality control of biological implants, tissue preparations or transplants, it is desirable to be able to characterize the culture tissue cells of the implant, for example, human cartilage cells, before application but also during culturing of the implant. The degree of differentiation and/or vitality of the cells should then be determined as a priority. This is of particularly great significance in implants from (autologous) human cells, since these cells can dedifferentiate during culturing, in which case they lose their tissue-specific properties desired for therapy. The quality of the implant diminishes on this account. Dedifferentiated cells also often have a tendency toward increased proliferation rate, for which reason they are viewed as potential cancer cells. Means and methods for characterization and typing of tissue cells and the extracellular matrix of the tissue and therefore for quality control of the biological implants are therefore desirable.

Quality control of biological implants is not uniformly regulated by law at present, since there is no known method that could be equally applied as gold standard to the wide variety of tissue cell types. It is known that immune cytological methods are used whose quality depends mostly on the specificity of the employed antibodies and which cannot be normalized or standardized. Known methods for characterization of biological material are "invasive" methods that make reuse of the investigated cells impossible. For example, in the known flow cytometry the cells are characterized by expression of certain surface molecules (CD antigen test). Based on this procedural deficiency only parts of the cultivated tissue can now be proposed as a biological implant for implantation. The other part must be "sacrificed" for invasive characterization of the cells. Means and methods are therefore desirable in which a noninvasive, nondestructive biological characterization of the cells being investigated can occur, if possible, in the liquid culture medium. It is also desirable to minimize the load on the tissue during the measurement.

Another aspect of the invention concerns sterility control in the production of drugs or active ingredients according to essentially biotechnological methods. In such methods active ingredients are produced by biological cells or cell systems, like microorganisms and/or tissue cells in so-called bioreactors. On an industrial scale bioreactors with volumes of 50 liters or more are used. Recovery of the active ingredients often requires culturing time in the reactors of several weeks. A multistage purification is generally connected to the bioreactor in the production chain, from which the desired active ingredient composition can ultimately be obtained.

It is then essential that no foreign contamination occur in the reactor charge and the sterility of the active ingredient composition recovered from the bioreactor is guaranteed. In known methods at the beginning and end of reactor culturing or at the end of the production change, the charge is checked for foreign contamination and sterility. In the case of contamination, the entire product volume must be discarded.

In known sterility tests biological samples are taken from the running production process in the form of small amounts of liquid, cultured according to conventional microbiological methods on a nutrient medium and then differentiated to determine the type of contamination. Results can only be expected with a delay of several days. A shortcoming is that the possibilities for regulatory intervention into the process are then limited. In most cases at least the employed resources for continuation of the production process between the time of liquid sampling and the time of positive detection of contamination are lost.

To improve the production process and avoid costs there is a requirement for continuous testing for sterility or contamination over the entire culturing time, during the entire production process and/or along the entire production chain. A rapid detection method is desirable that offers a short detection time and means to perform such a method. At the same time, high specificity and sensitivity should be present. Such a detection method should preferably also be suitable to clearly establish the type of contamination, i.e., especially to determine the contaminating microorganism. In addition to saving costs for the otherwise lost resources, a time saving would also be connected to this, since the contaminated process could be quickly terminated and a new process started in a timely fashion.

Raman spectroscopy is a known method that has been used thus far mostly in chemical analysis and surface characterization. The method is also being increasingly used for characterization of biological samples and in the investigation of biological fluids. When the biological sample is irradiated with excitation radiation of a certain wavelength or wavelength range, both elastic and inelastic scattering processes occur on the irradiated molecules in the sample. The main fraction of the introduced excitation light is elastically scattered in the sample (essentially so-called Rayleigh scattering). In addition, inelastic scattering to a smaller extent occurs on the molecules, so-called Raman scattered radiation. The Raman scattered radiation differs in energy content and therefore wavelength from the introduced excitation radiation. The Raman scattered radiation has both a fraction shifted toward shorter wavelengths (anti-Stokes lines) and a fraction of longer wavelengths (Stokes lines). The spectral distribution of the fraction of Raman scattered radiation shifted toward longer wavelengths is regularly understood as the Raman spectrum (Stokes lines). The Raman spectrum is mostly characteristic for the irradiated molecule or the molecule composition of the irradiated sample. With methods based mostly on statistical algorithms, such spectra can clearly be assigned to certain molecules of an irradiated sample so that molecule compositions, biological cells, cell compartments and some cellular structures can be characterized and if necessary specified.

In a method known from WO 2004/099763 A1 Raman spectroscopy is used to investigate and analyze biological cells in which the microorganisms being investigated are cultured, isolated, exposed to excitation radiation and the Raman scattered radiation emitted by the cells analyzed spectroscopically. From the recorded spectral distributions of the emitted Raman scattered radiation, the characteristic values for the corresponding microorganisms are recorded by statistical analyses, for example, certain bands in the spectrum, and compared with corresponding characteristics of known microorganisms stored in databases. The analysis method is invasive, since the microorganisms being investigated are released from the cell and prepared. Preculturing of the analyzed cells is not prescribed.

A drawback in this method is the invasive approach, which leads to destruction of the analyzed cells. Another drawback is the long measurement times connected with known Raman spectroscopic methods.

Starting from the prior art, the technical problem underlying the present invention consists mostly of providing means and methods for simple-to-handle, rapid, noninvasive, nondestructive detection and characterization of biological cells in biological samples, preferably cell combinations, tissues, cell suspensions or biological fluids.

BRIEF SUMMARY OF THE INVENTION

The present invention solves the underlying technical problem essentially by furnishing a method for analysis of a biological sample based on an optical-spectroscopic principle and comprising at least the following steps: the biological sample, which is preferably present as a liquid or mostly liquid sample (biological fluid) is fixed in a sample holder unit, preferably reversibly, i.e., removable again and noninvasively, i.e., secured; any particles contained in the biological sample are categorized by: photomicrographic recording of the biological sample and/or particles contained in the sample and analysis of the image data by means of an automatic sample recognition process; and the biological sample is analyzed by Raman spectroscopy, specifically within a measurement zone positionable in the area of the biological sample, by exciting or generating Raman scattered radiation in the measurement zone by focusing an excitation radiation and detecting the Raman scattered radiation emitted by the biological sample in the measurement zone and analyzing the spectral distribution of the Raman scattered radiation, in which at least one Raman spectrum of the biological sample is obtained.

The method is then characterized according to the invention by the fact that the measurement zone is automatically positioned at certain sections or particles of the biological sample by means of the results of photomicrographic categorization according to established criteria and Raman spectroscopic analysis restricted to the area of the at least one automatically positioned measurement zone.

The invention preferably proposes to restrict Raman spectroscopic analysis of the biological sample spatially to particles present there that pertain to a predetermined category. This preferably occurs according to the invention by positioning the measurement zone automatically on certain particles of the biological sample and conducting Raman spectroscopic analysis there. Categorization-controlled positioning of the measurement zone is repeated in a preferred variant several times for other areas of the sample and/or other category criteria.

In the context of the invention "biological sample" is understood to mean one or more biological cells, separately or in cell combinations, tissue, transplants, implants, organ and tissue replacement preparations and their parts. Mostly animal and human cells are considered here as biological cells, like tissue, embryonal cells or stem cells, bacterial cells and bacterial spores, mycoplasmas, fungal cells, hyphae and spores. The biological sample need not necessarily contain such cells; detection of cells potentially contained in a biological sample is an object of the present invention. The biological sample is a composition potentially containing at least one biological cell; this is also understood to mean clinical samples, biopsies, as well as liquid and mostly non-liquid biological samples from tissues, transplants, organ and tissue replacement preparations and their parts and residues of sterile filtration.

In the context of the invention "particle" is understood to mean a biological cell or part of a biological cell that can be present in a biological sample, for example, in the form of a fluid. "Particle" is also understood to mean all individualizable or categorizable cells or cell fragments that are present in biological samples, especially in cell combinations, tissues, transplants, implants, organ and tissue replacement preparations or their parts.

"Biological fluid" in the context of the invention is understood to mean a special form of a biological sample, a potentially nonsterile fluid or suspension or one contaminated with biological cells which mostly occurs in the context of culturing of biological cells. The biological cells present in such a biological fluid are not merely contaminants; they are also understood to mean the cultured biological cells, for example, tissue cells. The cells are then cultured as a cell combination or tissue or as a cell suspension. The biological fluid is preferably chosen from: mostly biologically produced, pharmaceutical active ingredients or active ingredient compositions, culture media of biofermenters, clinical samples, like blood, urine, fluid, cerebrospinal fluid, blood plasma, blood serum, lymph, aqueous humor, mucosal smears, bronchial lavage and the like, as well as liquid culture media and supernatants of tissue cultures, cultures of biological implants, organ and tissue replacement preparations including mostly transport media, thawing media, rinsing media and storage media.

The invention therefore permits an enormous time gain by combining photomicrographic image analysis with a spectroscopic analysis method, targeted and purposeful reduction of areas of the sample being analyzed microscopically. By categorization by photomicrographic image analysis of the biological sample the time-intensive Raman spectroscopic analysis of biological sample can be advantageously restricted spatially to specific measurement zones of the sample. The total analysis time relative to known methods is advantageously shortened substantially on this account. Depending on the application, the measurement time (time from entry of the biological sample to end of acquisition of measured data or to acquisition of the analysis result), the measurement time is shortened to 48, 24 and up to 12 hours.

It is then mostly prescribed that selection of the measurement zones, preferably by means of pre-established criteria, is carried out automatically in which selection is directed toward the aspects of essential interest in the corresponding analysis: If the question of analysis is primarily directed toward checking contamination of the sample with germs, preselection by means of categorization of germs detected in the microscopic image, like bacteria and fungal cells or spores, permits targeted spectroscopic analysis of such germs.

If the question of analysis is primarily directed toward characterization of vitality or the differentiation stage of tissue cells, preselection by categorization of tissue cells detected in microscopic image, for example, chondrocytes, permits targeted spectroscopic analysis of these cells for "vitality markers" or "tissue type markers" that are recognizable by means of specific characteristic values of the Raman spectrograms.

Photomicrographic categorization of particles preferably occurs in the categories "biological cell" and "nonbiological cell, artifact." Categorization within the category "biological cell" preferably occurs in the categories "bacterial cell," "fungal cell," "bacterial spore," "fungal spore" and "(human) tissue cell." Categorization in the category "(human) tissue cell" preferably occurs in the categories "vital cell" and "nonvital cell" and/or preferably in the categories "differentiated cell" and "dedifferentiated cell."

To generate the Raman scattered radiation an excitation radiation with a wavelength in the near-infrared, preferably of 785±60 nm or in the UV range of 200±50 nm is preferably used.

It is preferably prescribed that the excitation radiation focused in the form of the preferably linear excitation zone is moved during analysis, preferably in steps over the fixed particle. After each step a new measurement cycle is preferably conducted. The analysis data obtained in the individual consecutive measurement cycles of the Raman spectra recorded from the excitation zone are then combined to a position-resolved image of local Raman spectra. For this purpose a position-resolved spectral analysis of the Raman scattered radiation is preferably conducted according to the invention by separating the Raman scattered radiation of the excitation zone spectrally and detecting it by means of a two-dimensional CCD array detector.

The invention therefore preferably proposes to carry out spectral analysis of the Raman scattered radiation by sequential focusing of the excitation radiation in the form of several linear excitation zones [i . . . i+n] within the measurement zone on the biological sample. The measurement time of spectral analysis is even further shortened by linear focusing because parallel detection and recording of several local Raman spectra is possible simultaneously along the linear extent of the excitation zone.

Spectral analysis of the Raman scattered radiation is preferably conducted by a position-resolved spectral analysis by means of a two-dimensional CCD array detector, in which a (first) linear excitation zone i is imaged true to position along its longitudinal extent in the first dimension of the CCD array and the spectral distribution of the Raman scattered radiation from each point along the longitudinal extent of this (first) excitation zone is imaged in the second dimension of the CCD array and the local Raman spectra recorded separately resolved according to position.

The position-resolved spectral analysis of the entire measurement zone preferably occurs in an iterative process, the first family of local Raman spectra being recorded in the first measurement cycle in the first excitation zone i and a second family of local Raman spectra being recorded in a subsequent measurement cycle of a second excitation zone i+1 locally adjacent to the first excitation zone i. For this purpose the linear focus of the excitation radiation is moved between measurement cycles from a first position relative to the biological sample fixed in the measurement zone to a second position. Additional measurement cycles are repeated for additional locally adjacent excitation zones i+n, the linear focus always being guided to a next position between the measurement cycles. The families of local Raman spectra of all excitation zones [i . . . i+n] are then combined to an overall picture of the position-resolved spectral distribution pattern of the biological sample fixed in the measurement zone (line scan).

The invention proposes by means of microscopic image data of the particles to localize, characterize and optionally identify by sample comparison individual particles. The recorded image data are preferably analyzed geometrically, in which case image characteristics are obtained. Image analysis occurs in known fashion, preferably by software-implemented feature detectors and sample recognition. A first categorization or typing of the particles can mostly occur from the image characteristics.

It is also proposed that the image data be correlated with the local Raman spectra recorded parallel to the particle so localized. The Raman spectra of an optically localized particle are preferably used to characterize the particle. An individualized characterization and optionally identification of the particle based on characteristic Raman spectra, based on characteristic morphology and preferably from a combination of the findings obtained from image analysis and spectral analysis is characterized, specified and identified.

From the obtained microscopic image data and at least one Raman spectrum, in at least one additional step the biological sample or particles analyzed in the measurement zone are preferably characterized. This occurs in a preferred variant by determining typical characteristic values from the at least one Raman spectrum and comparison of the determined typical spectrum characteristic values with stored known spectrum characteristics. In another preferred variant, characterization occurs by determining typical characteristics from the photomicrographic image data and comparison of the determined image characteristics with stored known image characteristics. In another preferred variant, characterization occurs by combining the results of characteristic comparison of spectrum characteristics and image characteristics.

Characterization of the biological sample or particles contained in it preferably occurs according to pre-established criteria from comparison of the determined characteristics. Preferred parameters of characterization are: genus, species, degree of differentiation, vitality and chemical composition.

In a second aspect the invention provides an optical spectroscopic method for analysis of biological fluids comprising at least the following steps: preferably reversible fixation of the biological sample in a sample holder unit; categorization of any particles contained in the biological sample by: photomicrographic recording of the biological sample and/or the contained particles and analysis of the image data by an automatic sample recognition process; and Raman-spectroscopic analysis of biological sample within a measurement zone positionable in the area of the biological sample: Excitation of Raman scattered radiation by focusing of an excitation radiation in the measurement zone and detection of Raman scattered radiation emitted by the biological sample in the measurement zone and analysis of the spectral distribution of the Raman scattered radiation, in which at least one Raman spectrum of the biological sample is obtained, the method being characterized by the fact that reversible fixation of the biological sample occurs by flow through the sample holder unit of the biological sample or injection of the sample in it, in which case any particles contained in the biological sample are retained in the measurement zone and fixed there reversibly, at least for the duration of analysis. It is then proposed according to the invention that the biological sample be a biological fluid and the sample holder unit designed as a so-called fluid cell.

The particles are rinsed with the biological fluid in the fluid cell and retained or fixed there by appropriate means in the fluid cell. The invention proposes to detect and preferably additionally to characterize the retained or fixed particle or particles in the fluid cell by Raman spectroscopy, preferably additionally by optical microscopy, preferably as differential interphase contrast (DIC).

The method also proposes that the particles be precategorized in the fluid cell. This preferably occurs by: Separation of the particles according to size on several perforated plates with different perforation diameters connected in succession on the fluid cell in the direction of flow. The method therefore proposes a quasi two- or multistage preselection of those sample areas or particles before, after or simultaneously with the spectroscopic analysis of preselection. In this preferred variant of the invention preselection therefore occurs in a first stage according to size and in a last stage selection according to category.

In a preferred additional step detection of any contamination of the biological fluid occurs with reference to the spectrum and/or image characteristics determined according to the invention, in which sufficient agreement of the characteristics demonstrates presence of infectious particles in biological fluid and with lack of agreement of the characteristics absence in contamination of the biological fluid is detected.

The invention therefore proposes: A fluid cell is traversed with the biological fluid being analyzed and particles contained in the biological fluid, i.e., especially biological cells, are retained, preferably fixed in the fluid cell. This preferably occurs temporarily, preferably at least for the duration of analysis; for analysis the retained or fixed particles in the fluid cell are irradiated with excitation radiation which excites inelastic scattered radiation, i.e., Raman scattered radiation in the irradiated particles. For analysis the Raman scattered radiation emitted by the irradiated particles is detected and the spectral distribution of the Raman scattered radiation analyzed, during which at least one Raman spectrum is obtained. From the at least one Raman spectrum one and preferably several preferably characteristic values are determined and the determined characteristics are compared with known and stored characteristics, preferably according to known analysis methods.

The method according to the invention permits during sufficient agreement of the determined characteristics with the stored characteristics detection of the presence of particles preferably infectious particles, like bacteria, cells, bacterial spores, fungal cells or fungal spores in the biological fluid; in the absence of agreement of the characteristics, the absence of contamination of the biological fluid with infectious particles, i.e., sterility, is detected.

In another preferred variant of the method according to the invention, through the characteristic value comparison according to the invention, with sufficient agreement of certain characteristics the retained particles are characterized, i.e., the cell type, cell species and/or the degree of differentiation of the cell are determined so that the presence of a certain cell species or a cell with a certain degree of differentiation in a biological fluid is detected. The method according to the invention therefore advantageously serves for continuous sterility control in biological fluids and/or determination and characterization, especially the determination of degree of differentiation of any biological cells contained in a biological fluid.

The invention advantageously permits that both during drug development and during preparation of individual therapeutics, i.e., biological implants and tissue preparations, primary biological fluids can be investigated without changing or causing a deterioration in the composition of the investigated biological fluid. In particular, any particles contained in the biological fluid, i.e., particularly biological cells, especially tissue cells are not influenced in their vital functions and not disturbed in their integrity. This is made possible above all by the fact that biological cells can be measured in their "natural" environment, i.e., in the biological fluid that in most cases is the culturing medium of the cells, in which the cells are retained or fixed preferably exclusively for the duration of the measurement or analysis in the fluid cell proposed according to the invention.

The invention also permits that a Raman spectroscopic analysis can be conducted for detection and optionally characterization of biological cells contained in a biological fluid in a continuous production or culturing process, preferably continuously or quasicontinuously without having to remove parts or samples from the process and analyze them separately and then discard them. In a preferred variant the device according to the invention is therefore integrated in a production chain, preferably in a side stream so that during production or purification of biologically produced active ingredients, in the fermentation process or during culturing of tissue transplants, the sterility, presence of foreign contamination or the degree of cell differentiation can be continuously investigated.

There is also the advantage that during sterility control of tissue transplants already at the time of implantation in patients assertions can be made whether the implant is contaminated or not. During detection of contamination of already implanted preparations a differentiated diagnosis can be established in a comparatively short time and, if necessary, patients that are most probably ill can be deliberately treated against the determined pathogen. Another advantage is also the integration capability of the sterility test according to the invention, differentiated diagnosis and determination of the vitality or viability of cells and the implant in an arrangement or with a combined method so that in the case of autologous transplants the entire necessary bandwidth of the analysis methods is covered.

The method according to the invention preferably proposes that any particles contained in the biological fluid to be analyzed are held in the fluid cell by at least one perforated plate arranged in the fluid cell with one or more perforations. These perforations are preferably arranged in structured fashion in the perforated plate. The comments made below are referred to here. The method proposes with particular preference that the particles are retained from the biological fluid on the top of the perforated plate. This is preferably guaranteed by the fact that by applying a partial vacuum to the opposite side of the perforated plate, the particles present in the biological fluid are seemingly "sucked" onto the perforations on the top of the perforated plate and fixed in the area of or on the perforations. The particles are at least temporarily fixed on the perforated plate according to the invention; preferably at least for the duration of analysis. This is preferably achieved by the fact that the partial vacuum is applied roughly for the duration of fixation.

The method further proposes that the particles in the fluid cell be retained by at least one perforated plate arranged in the fluid cell with one or more perforations. The particles are preferably fixed from the biological fluid on the "top" of the perforated plate by, optionally temporary, application of a dynamic and/or static pressure gradient in the direction of the opposite "bottom" of the perforated plate. This will be understood to mean that a pressure difference is produced between the top of the perforated plate and the opposite bottom of the perforated plate, which communicate via the at least one perforation provided in the perforated plate. This is achieved in a preferred variant in that at least part of the biological fluid containing the particles situated or flowing past the top of the perforated plate is drawn downward via the at least one perforation over the perforated plate. In an alternative variant the pressurized biological fluid on the top of the perforated plate is at least partially drained downward via the at least one perforation over the perforated plate. Application of the partial vacuum preferably occurs in an operating state in which the biological fluid traverses the fluid cell and therefore flows along the top of the perforated plate. In an alternative variant the partial vacuum is applied in an operating state in which no net flow of the biological fluid occurs through the fluid cell and along the surface of the perforated plates.

In a preferred alternative or additional variant the biological fluid traverses the perforated plate in a main stream so that any particles contained in the biological fluid are fixed according to the geometric conditions of the perforation diameter and particle size on the upstream side of the perforated plate being "filtered" from the biological fluid. One skilled in the art, depending on the area of application and the specific geometric structure of the fluid cell will select the appropriate method or several preferred method variants in combination without departing from the teachings of the present invention.

The excitation radiation is preferably focused on at least one particle retained in the fluid cell in a local excitation zone. This excitation zone with particular preference is linear (line focus) so that a series of particles retained or fixed in the measurement zone, i.e., in the fluid cell or culture dish, are simultaneously excited next to each other for emission of the Raman scattered radiation.

The technical problem underlying the invention is also solved by furnishing of a device that is especially suited for execution of the aforementioned method. The procedures, parameters and process steps described in conjunction with the following devices are also preferred features of the method described above.

The device for optical-spectroscopic analysis of biological samples according to this invention pertains to at least the following elements:

sample holder unit for fixation of the biological sample in a measurement zone;

excitation radiation unit suitable for excitation of Raman scattered radiation by means of excitation radiation in an excitation zone within the measurement zone; and analysis unit appropriate for spectral analysis of the Raman scattered radiation emitted in the excitation zone of the biological sample.

The device is preferably characterized by the fact that the biological sample is a biological fluid and the sample holder unit is a fluid cell traversable by the biological sample in which the fluid cell has means that are suitable for retaining and reversible temporary fixation of any particles contained in the biological sample in a measurement zone of the fluid cell.

The device therefore contains at least the following elements: at least one fluid cell, which can be traversed by the biological sample in the form of a biological fluid, in which the fluid cell has at least one means for temporary retention, especially fixation of the particles; the particles are immobilized on the means at least for the duration of spectroscopic and optionally microscopic analysis; at least one excitation radiation unit, which is capable of generating excitation radiation so that Raman scattered radiation could be excited in the particles retained or fixed in the fluid cell; at least one analysis unit that is suitable for spectrally separating the Raman scattered radiation emitted by the particles and recording the Raman spectrum (spectral analysis).

According to this aspect of the invention the fluid cell is preferably configured so that particles entering the fluid cell with the biological sample, i.e., possible biological cells as contaminants or tissue cells, but also possible artifacts, can be retained in the fluid cell and especially fixed there at a specific position. This is preferably made possible by at least one perforated plate or perforation array provided in the fluid cell with one and preferably several perforations or pores, preferably so-called micropores. The perforations or pores preferably have a circular or almost circular cross section. In a preferred variant the perforations are made linear or gap-like. The perforated plate is then as capable as a filter mesh to retain particles from the liquid biological sample flowing through the fluid cell. The diameter or dimensions of the perforations in the perforated plate are preferably chosen so that particles or biological cells cannot pass through the perforations because of their size and can be retained in the fluid cell. At least one, preferably precisely one such particle can be retained or fixed in an individual perforation.

The fluid cell according to the invention is characterized in particular by the fact that at least one perforated plate or perforation array has perforations arranged in structured fashion. The perforations are preferably arranged in a regular pattern (array), in which the ratio of average spacing of the perforations to each other (hole spacing, grid dimension) to the diameter of the perforation is chosen so that on one, preferably on each individual perforation, at least one preferably precisely one particle can be retained. This grid size/diameter ratio is preferably 1.1 to 20, especially 5 to 15 and more particularly about 10. The perforated plate is preferably designed so that the perforations or pores are arranged therein the form of a regular addressable array, in lines and columns. At a size of the perforation array of about 1.6 cm$^2$ (about 0.5 by 0.5 inch) about 10$^6$ perforations are preferably arranged in the form of microholes; at a pore diameter of 1 μm the grid size is about 12 μm. This guarantees that the biological cell or particle fixed on a pore does not overlap a cell or particle fixed on a neighboring pore so that both cells or particles can be separately analyzed optically. It is understood that in perforated plates the hole grids assume smaller values for fixation of small biological cells like bacteria than in perforated plates for fixation of large (human) mammalian cells. In one variant the holes have a diameter of 1 μm and the surface of the hole array is 10 mm$^2$ (10 by 10 mm). In a hole grid of 10 μm there are about 1,002,000 holes in the hole array. This hole array mostly serves for retention or fixation of bacterial cells, fungal spores and the like. Such perforated plates preferably have a diameter of the perforations in the range from 1 μm or smaller, the preferred lower limit being 0.2 μm. The preferred hole grid is from 2 to 15 μm, preferably about 10 to 12 μm.

In other preferred variant of a perforated plate the holes have a diameter of 2 μm and a hole grid of 20 μm. This hole array mostly serves for retention or fixation of tissue cells of animal or human origin. Such perforated plates preferably have a diameter of the perforations of 2 μm or larger, preferably about 2 to 6 μm. The preferred hole grid is 15 μm or more, preferably about 15 to 50 μm.

The dimensioning of the perforated plate appropriate for the corresponding application is determined by one skilled in the art within the limits stipulated according to the invention ultimately according to the fluid properties of the biological fluid being investigated and with reference to the particle being analyzed.

In a preferred variant the fluid cell at least has a second or additional such perforated plate. This or these is or are arranged upstream of the first perforated plate in the fluid cell relative to the direction of flow of the biological sample. The second or additional perforated plate also has one and preferably several perforations. For arrangement of the perforations in the second or additional perforated plate that which was described above in conjunction with the first perforated plate applies. The diameter of the perforations of the second or additional perforated plate is preferably greater than the diameter of the perforations of the first perforated plate. The ratio of first diameter of the perforations of the first perforated plate and second diameter of the perforations of the second and optionally additional perforated plate is preferably chosen so that large particles contained in the biological fluid, for example, human cells, can be retained by the second and optionally additional second perforated plate, while smaller particles, like bacterial cells, bacterial spores, mycoplasms, fungal cells or fungal spores, can pass through the second and optionally additional perforated plate and can be retained (downstream) in the first perforated plate.

The first, second and optionally additional perforated plates or perforation array are preferably arranged essentially parallel to each other. Through this regular filter or sieve arrangement within the fluid cell it is possible to separate the particles contained in the biological fluid according to size and arrange them in different separated first, second and optionally additional levels lying one above the other that are formed by the perforated plates in the fluid cell. This permits the particles retained according to size to be investigated separately and preferably to be investigated by Raman spectroscopy and also by light microscopy.

At least the first perforated plate (lying downstream) or hole array is preferably arranged parallel to the net direction of flow of the biological fluid (the angle of the surface normal of the perforated plate to the vector of net flow is about 90°) so that particles present in the sample fluid in a first operating state of the fluid cell can move along the top of the perforated plate and in a second operating state the particles can be retained preferably by a partial vacuum that can be applied on the opposite side of the perforated plate from the overflowing fluid and fixed on the perforations on the top of the perforated plate. It is preferred that the particles retainable in the fluid cell can be arranged next to each other, especially in one plane.

The fluid cell is preferably equipped with a first and at least a second perforated plate or perforation array so that particles with a size of at least 2 µm are fixed in the plane formed by the second perforated plate and can be arranged in a line so that measurement of the cells can occur in the focus of the excitation radiation. Particles with a size of less than 2 µm and larger than 1 µm can be fixed in the downstream first perforated plate, which have already passed through the second perforated plate. These are mostly bacteria, fungi, mycoplasmas as well as bacterial spores and fungal spores, all of which as "infectious particles" can indicate the contamination of investigated biological fluid. In this variant of the apparatus according to the invention it is proposed that the excitation radiation can be focused on the particles retainable in the downstream ("lower") first perforated plate. It is advantageously possible in a single measurement arrangement to analyze both larger particles, for example, tissue cells of human origin and smaller particles separated from them, mostly microorganisms like bacteria, fungi, spores in a liquid biological sample.

In a preferred additional variant of this aspect of the invention a microfluidic flow channel is provided in the fluid cell. This flow channel is configured so that particles present in the biological sample fluid can migrate sequentially or mostly sequentially through the flow channel when and if the fluid cell is traversed by the biological sample and the particles can be fed in series to an optics for classification and characterization. A preferred temporary holding of the particles in the fluid cell for analysis is mostly made possible by stopping the net flow of the biological fluid through the fluid cell. The particles present in the biological fluid are preferably arranged one behind the other, preferably directly behind each other or essentially at a regular spacing from each other in the microfluidic flow channel. The channel width is adapted to the size of the focus of the optics. Devices to generate force fields, preferably chosen from sound fields and electromagnetic fields are preferably additionally provided in the channel in order to keep the particles in position during performance of the measurement method. One skilled in the art is familiar with the principles of microfluidics and will dimension such a flow channel easily so that it satisfies the function prescribed according to the invention.

In a preferred variant several microfluidic channels preferably at regular spacing and arranged parallel to each other are provided in the fluid cell. It is then preferred that at least two of the several flow channels differ from each other in dimension and/or configuration so the different microfluidic conditions can prevail in these channels. This design is preferably suitable for separating different particles occurring in the biological fluid according to the microscopic or physical properties to categorize them and optionally analyze them separately. At least one flow channel is connected in a fluid cell after a perforated plate or a perforation array according to the invention, to which essentially just the particles and preferably exclusively the particles that are smaller than the holes of the perforated plate are fed in series to an optics for classification and characterization.

According to another aspect of the invention the sample holder unit of the device according to the invention is designed as a culture dish with thin optically transparent material so that focusing of the excitation radiation could occur in the biological sample. In a preferred variant an ordinary cell culture plate open on the top or cell culture plate for microscopy or a Petri dish with a thin optically nonrefractive plastic or glass bottom is provided as sample holder unit for analysis of a small tissue sample (from 1 to 2 $mm^2$).

It is therefore prescribed that at least the parts of the fluid cell or culture disk lying in the beam path of the device according to the invention are made from radiation transparent or light transparent material. Preferred materials are chosen from: silicate glass, quartz glass, silicon glass, silicon dioxide glass, silicon nitride glass, calcium fluoride glass, barium fluoride glass, zinc selenide glass, zinc sulfide glass and germanium glass. Silicon nitride is especially preferred here. The invention is not restricted to these materials; one skilled in the art will consider similar materials suitable for the purpose, especially all optically clear, if possible only slightly refracting, if possible only slightly chromatically dispersing materials as well as materials as transparent as possible in the wavelength range of the excitation radiation and in the range of the emitted Raman scattered radiation and the radiation to be detected. These are encompassed by the teachings according to the invention. Such additional materials include synthetic polymers, like polyacrylics, polyethylenes, ethylene/propylene copolymers, polystyrenes, polyamides and polycarbonates.

It is also prescribed to coat or enrich the sample holder unit on the surface with metal or metal colloids and specifically at least in the contact area with the biological sample or the perforated plate of the fluid cell, at least in the area of the perforations or pores, where the particles could be retained, with metal or metal colloids. Bonding of the metal occurs in known fashion preferably by local derivatization of the surface. Enrichment of the culture dish surface or perforated plate surface with gold colloids is particularly preferred. In order to improve Raman spectroscopic analysis of particles retained in the area of the perforations relative to particles situated elsewhere on or in the area of the perforated plate, it is proposed to apply the metal or metal colloids alone in the area of the perforations on the perforated plate.

The electronic properties of the metals are suitable for increasing the Raman emissions of the irradiated biological sample, biological cell or retained and fixed particles (SERS, surface-enhanced Raman spectroscopy). By the increase in intensity according to known principles the integration time of detection could be shortened. This represents an additional aspect of the solution according to the invention for shortening the measurement or analysis time. In addition, the combination with SERS permits an improvement in signal/noise ratio and therefore detection of the additional possible characteristic bands in the Raman spectrum.

The excitation radiation unit preferably has at least one light source to generate the excitation radiation. This light source is preferably at least one laser with almost monochromatic emission spectrum. As an alternative the light source is a gas discharge lamp and/or an incandescent emission lamp, for example, a tungsten lamp or Nernst pin, in which an appropriate monochromator, for example, an optical grating or combination of several optical gratings are preferably connected to narrow the emission spectrum of these lamps. The excitation radiation unit preferably has so-called plasma line filters or corresponding means to filter the main wavelength. The excitation radiation unit also preferably has at least one so-called band pass filter or corresponding means for parallelization of the laser light.

In a preferred variant the excitation radiation has a spectral distribution in the near-infrared range. Wavelengths from 700 to 1200 nm are preferred. The excitation radiation preferably has a wavelength of about 785±60 nm, more preferably 785±30 nm, 785±10 nm and most preferably about 785 nm. Without being bonded to the theory, this wavelength range for Raman spectroscopy of living biological cells in liquid media or in cell combinations or tissues has a number of advantages: Absorption of the excitation radiation in the liquid medium is tolerably low, the undesired emission of fluorescence radiation is tolerably low, the damaging effect on the structure and light function of the irradiated living cells is minimal. At the same time the Raman scattered radiation excited in this wavelength range facilitates recording of cell-specific Raman spectra (so-called fingerprint range).

In another variant of the invention excitation radiation in the UV range is prescribed. Preferred wavelengths are 200±50 nm. The subsequent comments therefore also apply to UV-Raman spectroscopy in which radiation intensities, choice of material of the optical media and detector sensitivities are adapted accordingly relative to IR spectroscopy.

In order to further reduce the measurement time for detection and recording of the Raman spectrum (time integration), an excitation radiation of higher intensity should be used if possible. This is achieved preferably by using a high energy laser with an excitation energy of more than 50 mW, especially in the range from 50 to 500 mW. In a preferred variant a laser of about 100 mW is used. Diode lasers are preferred. One skilled in the art is aware that the radiation energy acting on the irradiated particles depends on the specifically employed optical system and the optical arrangement. Depending on the optical design, light sources with higher or correspondingly lower radiation energy are required. The radiation energy acting on the biological cell during measurement is limited downward by the measurement time and the signal/noise ratio of the employed detector for Raman scattered radiation: It is limited upward by the disadvantageous effects on integrity and life function of the irradiated cell that occur at higher energy. Radiation energies (calculated for the position of the irradiated cell and integrated over the exposure time) of at least about 10 Joule to a maximum of 300 Joule, preferably about 100 to 200 Joule, are preferred.

The device preferably has at least one line focusing unit. This is suitable for focusing of the excitation radiation produced in the excitation radiation unit on the biological sample, especially on the biological cells or particles to be analyzed in the sample, in the form of an essentially linear excitation zone.

The device according to the invention thus has the advantage of reducing the measurement times, since several points can be measured simultaneously along the linear excitation zone. It is therefore proposed to reduce the laser power accordingly so that the investigated living biological cells are even better protected. Line focusing simultaneously permits position-resolved measurement by means of so-called line scan so that ultimately individual particles or biological cells can be analyzed in individualized fashion in the measurement zone.

The line focus is preferably implemented by means of at least one cylindrical lens in the beam path of the excitation radiation. One skilled in the art will recognize that additional measures to generate a line focus are also suitable, to produce the line focusing arrangement proposed according to the invention.

The line focusing arrangement preferably has at least one so-called beam expander for improved focusing of the excitation radiation. The focusing arrangement is preferably designed so that the focused beam of the excitation radiation impinges on the surface normal of the measurement zone at an angle of 30° or less.

The line focusing arrangement is preferably suitable for moving the linear excitation zone over the particles or biological cells arranged fixed in the measurement zone. This is made possible by at least one scanner unit provided on the line focusing arrangement which is designed in known fashion. One skilled in the art is familiar with appropriate measures and means for implementing such a scanner unit. The line focusing arrangement is preferably connected to the scanner unit so that movement of the linear excitation zone is essentially perpendicular to its longitudinal extent. An acoustooptically tunable filter (AOTF) is preferably used as scanner unit. This has no moving optical parts according to design and function. In a preferred variant the measurement zone is movable with the particles or biological cells relative to a fixed focusing beam. This is preferably implemented by a motorized sample holder or object stage to which the culture dish is connected. Piezo-operated systems are suitable here.

In a preferred variant the analysis unit according to the invention is a CCD (charge coupled device)-based Raman spectrograph containing at least the following elements:

- at least one optical grating or similar means for spectral separation of the Raman scattered radiation emitted in the excitation zone;
- at least a two-dimensional CCD array for position-resolved electrical detection, optionally for imaging recording of the spectrally-separated scattered radiation; and
- at least one optical arrangement for imaging of the spectrally separated scattered radiation on the two-dimensional CCD array.

The analysis unit is preferably designed as a Raman spectrograph according to Czerny-Turner. As an alternative the Raman spectrograph is preferably a lens-based system. The analysis unit is preferably characterized by the fact that the optical arrangement for position-resolved imaging of the spectrally separated scattered radiation of a linear excitation zone is imaged on the two-dimensional CCD array so that in the first dimension of the CCD array the preferably linear excitation zone is imaged true to position along this longitudinal extent and in the second dimension of the CCD array, the spectral distribution of the scattered radiation is imaged from each point along the longitudinal extent of the linear excitation zone. This design advantageously permits, especially in conjunction with the line scanning method, a position-resolved reproduction of the measurement zone in which the particles or biological cells being analyzed are arranged. Representation of the data of the local Raman spectra of the particles or biological sample in the measurement zone true to position occurs in the form of a three- and preferably four-dimensional array in which the first two dimensions correspond to the width and longitudinal extent of the measurement zone. In the third and optionally fourth dimension the local Raman spectra from each position of the analyzed area are recorded in the form of a characteristic value or "band" (third dimension) or preferably the spectral distribution of intensity (third dimension) according to the wavelength or wavenumber (fourth dimension), preferably in relation to excitation wavelength. For this purpose the local Raman spectra (third and fourth dimension) are simultaneously recorded for the positions along the longitudinal extent (second dimension) of the first excitation zone in the line scanning method in a first measurement cycle. In additional measurement cycles this can be continued for a second and any additional excitation zone along the width extent (first dimension) of the entire measurement zone.

The CCD array (CCD chip) provided in the analysis unit for recording/detection and analysis of emitted Raman scattered radiation is preferably designed so that it is particularly sensitive for the near-infrared range or for a spectral range with a wavenumber of 200 to 3500 cm$^{-1}$. One skilled in the art will propose known measures for this purpose. Designs of the CCD array with rapid measurement time (integration time) at good signal/noise ratio are preferred, especially so-called open electrode CCD, a back-thinned CCD, deep depletion CCD or an electron multiplier CCD. In order to improve the signal/noise ratio the CCD array is preferably cooled; preferred cooling temperatures are about $-50°$ C. to about $-100°$ C.

According to one aspect of the invention the device preferably has at least one microscope-optic unit or device, i.e., microscope unit, for imaging microscopic or photomicrographic analysis of the particles retained or fixed in the measurement zone according to the invention. This optical unit is preferably a transmission microscope with preferably alternately switchable phase contrast optics, preferably for differential interface contrast microscopy (DIS), with particular preference a fluorescence microscope.

The microscope unit preferably has optics that possess sufficient transmission in the wavelength range of the excitation radiation and in the wavelength range of the emitted Raman scattered radiation, especially optimized for this wavelength range. Preferably the excitation radiation unit is coupled via appropriate means into the beam path of the microscope unit. For example, the light source usually provided on a fluorescence microscope to generate fluorescence is supplemented or replaced by the excitation radiation unit according to the invention.

Through appropriate optical means, especially blocking filters, it is preferably guaranteed that the excitation radiation in the microscope unit is separated from the observation beam path and from the illumination beam path of the imaging part of the microscope unit and from the beam path from the emitted Raman scattered radiation preferably recorded by the microscope unit. It therefore becomes possible to integrate the device according to the invention in ordinary microscope systems. The analysis unit appropriate for analysis of the spectral distribution of the Raman scattered radiation is also preferably integrated in the microscope unit. This is preferably accomplished by coupling the analysis unit in appropriate fashion into the observation beam path, for example, camera connection.

In addition to the excitation radiation unit, at least one additional illumination source for production of microscope images, especially a light source for fluorescence microscopy [can be integrated] on the microscope unit. This is typically a high pressure mercury vapor lamp. The microscope unit is preferably equipped with known filters for performance of fluorescence microscopy.

The microscope unit is also equipped with at least one image recording unit, preferably a CCD camera with appropriate optics for recording and later analysis of microscope images obtained from the particles arranged in the measurement zone of the device or biological cells. The image recording unit with particular preference is connected to a provided computer unit that is suitable, optionally by means of appropriate image analysis algorithms, for analyzing the microscope images of the particles or biological cells recorded with the microscope unit and displaying and/or storing the results of analysis.

In a preferred variant the device has at least one computer unit. This is preferably connected at least to the analysis unit for analysis of the emitted Raman scattered radiation. The computer device is also suitable for determination of characteristics of the recorded Raman spectra (spectrum characteristics) and the characteristics of the recorded microscope images of the particles (image characteristics). The computer is also suitable for comparison of the determined spectrum characteristics or image characteristics with stored, preferably predetermined spectrum characteristics or image characteristics. The device preferably also has at least one memory element, which is suitable especially for storage of the stored characteristics, the characteristics determined in the computer device and the results of the characteristic comparison performed in the computer unit. The device also preferably has at least one output element, preferably a display element, which is suitable for displaying at least one result of the characteristic comparison, which includes categorization, typing, characterization and/or specification of the analyzed particle or particles. At least one result of the immediately performed characteristic comparison is then preferably displayed. As an alternative, results of a preceding characteristic comparison stored in the at least one memory element are output or displayed. The device is also preferably suitable for displaying the microscope image of the analyzed particles, optionally together with the results of the characteristic comparison and/or the Raman spectra.

The computer device is also suitable for calculating the results of image analysis with the results of characteristic analysis of the Raman spectra so that a clear characterization of the particles retained from the biological fluid of the fluid cell, i.e., especially the biological cells, is made possible. The at least one memory element is preferably also suitable for storing the results of image analysis and the results of calculation of the results of image analysis with the results of the characteristic comparison of the Raman spectra. The at least one output or display unit is preferably also suitable for output or display of the results of optical image analysis and/or the results of calculation of the results of optical image analysis with the results of characteristic comparison of the Raman spectra and specifically both the current results and also results of previous measurements or analyses optionally scored in the at least one memory unit.

Through the evaluation of the microscope images conducted according to the invention it is advantageously made possible to assign the position-resolved recorded local Raman spectra to certain particles localized via the microscope image data. In this way an assertion can be made concerning the distribution, arrangement and frequency of certain particles, preferably tissue cells in the biological sample, i.e., especially in the analyzed tissue section, cell combination or implant.

Another object of the invention is the use of the already described device according to the invention and/or use of the already described method according to the invention for the following preferred applications or their combinations:

Use for noninvasive, nondestructive control of biological samples, preferably fluids for sterility and/or contamination;

Use for noninvasive, nondestructive characterization or typing and/or selection of biological cells contained in a biological sample;

Use for noninvasive, nondestructive characterization of differentiation status of biological cells contained in the biological sample;

Use for noninvasive, nondestructive characterization of typing of allogenic or autologous implants.

BRIEF DESCRIPTION OF THE DRAWINGS

The invention will now be further characterized by the following FIGS. 1 and 2 and the subsequent application example without this being understood to be restrictive relative to the teaching of the invention.

DETAILED DESCRIPTION OF THE INVENTION

Figure 1:
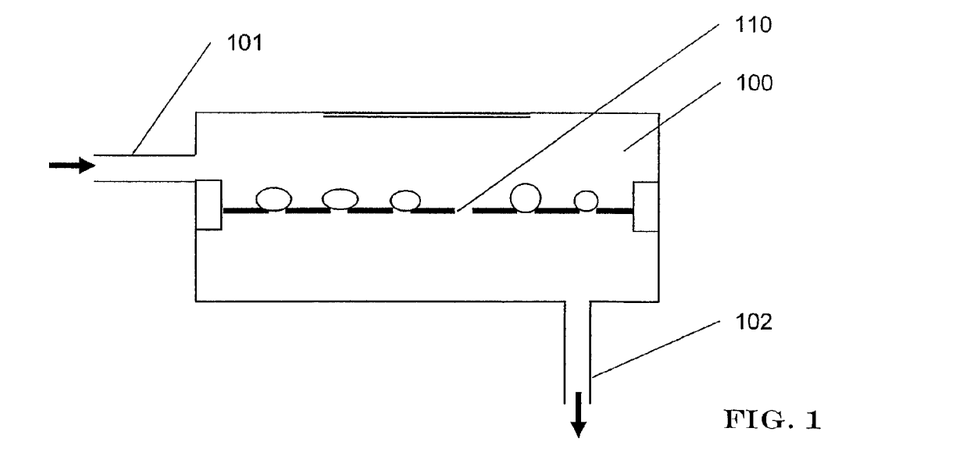
FIG. 1 shows the schematic layout of a fluid cell (100) according to the invention with a perforated plate (110) arranged in the fluid cell with perforations (115) with at least one inflow (101) for the biological fluid and at least one outflow (102). Schematically the particles retained on the perforated plate from the biological fluid and the net flow (arrow) along the pressure gradient are illustrated.
Figure 2:
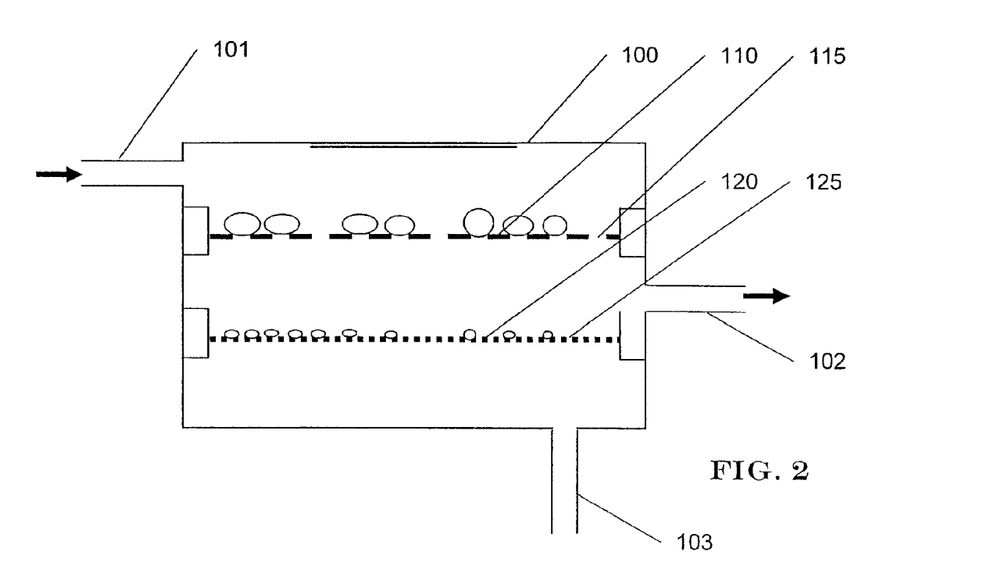
FIG. 2 shows the schematic layout of another fluid cell (100) according to the invention with two perforated plates (110, 120) arranged parallel and one above the other in the fluid cell with perforations (115, 125) with at least one inflow (101) for the biological fluid and at least one outflow (102) as well as at least one additional connection (103) on the bottom of the downstream first perforated plate (110) for application of a partial vacuum relative to the top of the perforated plate. The particles retained on the perforated plates (110, 120) from the biological fluid and the net flow (arrow) are illustrated schematically.

Practical Example: Sterility and Quality Control of a Transplant from Autologous Cartilage Biopsies
Material:
Apparatus: Sterile glass pipettes (5 or 10 mL, Eppendorf Co.); sterile syringe; safety workbench (HERAsave, class II, Heraeus Co.); centrifuge (5810R, Eppendorf Co.); device according to the invention with a light and phase contrast microscope as well as Raman spectroscope with fluid cell; gassing incubator (BBD 6220, Heraeus Co.)
Solutions: Collagenase (Worthington Biochemicals); autologous human serum (extraction from the patient's own blood sample)
Transplant: Autologous cartilage biopsy from the patient
Transport of the biopsy occurs in a transport medium that also functions as nutrient medium for the contained cells in the biopsy. This storage of the cartilage tissue occurs for 24 to 48 hours at 8° C.
Performance:
1.1 Analysis of a Liquid Biological Sample
1. Pipetting and investigation of the supernatant of the transport medium in the transport container or an aliquot from the supernatant (usually 10% of the total supernatant). With a prefilter all particles that are significantly larger than bacteria and fungal spores (for example, greater than 3 µm) are optionally filtered out before analysis of the sample fluid in the fluid cell by means of a microhole array.
2. The sample is injected under sterile conditions into the fluid cell (under the sterile bench, using a sterile syringe), optionally via one or two septa on an injection site of the fluid cell. The fluid cell is optionally directly connected to the transport container.
3. The microholes of the perforated plate (hole array; filter chip) in the fluid cell are traversed by the sample fluid or as an alternative overflowed. The size of the micropores is chosen so that the particles, bacterial cells, fungal spores, etc. relevant to the analysis cannot pass through the holes and are positioned on them:

In a first example of a fluid cell the holes have a diameter of 1 µm and the surface of the hole array has a size of 10 mm by 10 mm. 1,002,001 holes are found in the hole array with a hole grid of 10 µm.

In a second example of a fluid cell, hole arrays with different hole sizes (2 µm and 1 µm) are connected one behind the other in order to increase either the number of particles that can be characterized spectroscopically as a maximum or to preclassify the particles before optical and spectroscopic characterization or classification according to an individual feature (smaller than 2 µm or greater than or equal to 2 µm).

In a third example of a fluid cell a flow channel is connected after a hole array, to which the particles that are smaller than the holes of the hole array are fed in series to an optics for classification and characterization. The channel width is adjusted to the size of the focus of the optics. Optionally the particles are held in position during characterization by a device for generating force fields (sound fields, electromagnetic fields).

Positioning of the particles on the array-like holes occurs in this way.

4. In a subsequent step microscopy of the particles arranged in the measurement zone of the fluid cell occurs and distinction/categorization of human cells, bacteria, fungi, spores and other particles, as well as artifacts via the image analysis software. Image evaluation also serves for localization of the particles/cells in the measurement zone.

Recording of a Raman spectrum of the cell-free part of the transport medium is optionally carried out as a reference for extraction of the actual Raman signal of the sample or cells.

5. Raman spectroscopic investigation of the localized cells for distinction of cell types (here: chondrocytes and fibroblasts) and other microorganisms (for example, *Clostridium sporogenes* (DSM 1664), *Escherichia coli* (DSM 498), *Bacillus subtilis* (DSM 347), *Staphylococcus aureus* (DSM 799, 346), *Pseudomonas aeruginosa* (DSM 1128), *Aspergillus niger* (DSM 1957), *Candida albicans* (DSM 1386)) by means of reference spectra from the database and comparison of the obtained spectra with the corresponding references (characteristics, characteristic parameters, indicator bands).

A first control of the state or quality of the cells optionally occurs, especially chondrocytes in the preparation by means of previously obtained reference spectrum of vital cells.

Duration of measurement: about 1 to 48 hours depending on the necessary requirements. For example, control of sterility occurs in addition to Raman spectroscopy, via microscope evaluation of the particles contained in the sample and the duration is 1 to 12 hours here. Assignment of any contamination and control of cell viability then occurs as required over a period from 2 to 36 hours.

1.2 Sterility Test of Blood Serum

After centrifuging of hematocrit (the solid blood components) from the blood sample taken from the organ/tissue donor to obtain analogous blood serum, which is added to the nutrient medium for the cell culture of the implant, a sterility test of the blood serum or an aliquot from it (10% of the serum is standard) is carried out in the fluid cell according to steps 1 to 5 under point 1.1. Duration of measurement: about 1-12 hours.

Recovery of the autologous blood serum occurs by centrifuging of hematocrit (the solid blood components). This serum is then added to the nutrient medium for the culture of the cells of the implant. Parallel with the additional steps a blood sample for further serological tests is sent to an external site in order to rule out viruses (for example, HIV) and contamination with bacterial toxins (for example, via an LAL test for general detection of endotoxins).

1.3 In-Process Control of Transplant Quality

If detection of contamination is negative and the obtained cells prove to be within the specifications for vital cells according to the reference spectra, reculturing of the isolated cells and buildup of the autologous transplant occur.

After isolation of the tissue-specific cells by collagenases, transfer of the cells to nutrient medium with 10% patient serum, they are cast into a native collagen matrix (Ars Arthro Co.). Culturing begins in the incubator (for example, temperature 37° C. and $CO_2$ content 5% for optimal and constant culturing conditions); the total culturing time is generally 10 to 14 days.

After the first 5 to 7 days in-process control of a sample from the supernatant of the culture medium occurs for sterility, tissue-specific cells and viability of the transplant. The procedure then occurs according to point 1.1.

1.4 Analysis of ECM

In addition, during culturing a first analysis of the matrix occurs (ECM) in which the cells are embedded. The matrix in which the cells are embedded, for example, mostly consist of isolated collagen type I. In the culture, however, an intrinsic matrix is formed around the vital chondrocytes after a certain time, which consists mostly of collagen type II. These two collagen types are distinguishable in the Raman spectrum.

For this purpose the dissolved fractions in the supernatant of the culture medium are analyzed spectroscopically in the device according to the invention.

1.5 Analysis of the Total Preparation

As a supplement to 1.1 to 1.4 individual cells on the surface of the transplant are categorized as vital or nonvital by means of the reference spectra. These measurements occur directly on the entire transplants, directly in the culture dishes as sample holder units according to the invention. For this purpose the culture dish is removed, mounted on the device according to the invention and measured.

1.6 Final Control

After production of the transplant a final control is necessary, which follows the procedure described in point 1.4.

Results:

The measurement time is reduced here to 24 hours. The speed achieved according to the invention is a critical advantage, since the transplant can be implanted within 24 to 48 hours in the patient and the functional capability of the cells retained. In the final control according to the invention it is known at the time of implantation in the patient that the implant is not contaminated.

The invention claimed is:

1. A method for optical-spectroscopic analysis of a biological sample in liquids, comprising:
   fixation of the biological sample in a sample holding unit;
   categorization of any particles contained in the biological sample by analysis of photomicrograph image data of the biological sample and/or particles contained in the biological sample; and
   Raman spectroscopic analysis of the biological sample within a measurement zone that can be positioned in the area of the biological sample;
   wherein the measurement zone is automatically positioned on certain sections or particles of the biological sample based on results of the categorization according to established criteria and the Raman spectroscopic analysis is restricted to the area of the measurement zone
   wherein a reversible fixation of the biological sample occurs by allowing the biological sample to flow through the sample holder unit, in which any particles contained in the biological sample are retained in the measurement zone and reversibly fixed there at least for the duration of the analysis, wherein the biological sample is a biological fluid and the sample holder unit is designed as a fluid cell; and
   wherein the particles in the fluid cell are retained by at least one perforated plate arranged in a fluid cell with one or more perforations.

2. The method according to claim 1, wherein the measurement zone is positioned on at least one particle present in the sample that belongs to a predetermined category.

3. The method according to claim 1, wherein categorization of the particle occurs in the categories "biological cell" and "nonbiological cell, artifact."

4. The method according to claim 3, wherein categorization in the category "biological cell" occurs in the categories "bacterial cell, fungus cell, bacterial spore, fungal spore" and "(human) tissue cell."

5. The method according to claim 4, wherein categorization in the category "(human) tissue cells" occurs in the categories "vital cell" and "nonvital cell."

6. The method according to claim 4 or 5, wherein categorization in the category "(human) tissue cells" occurs in the categories "differentiated cell" and "dedifferentiated cell."

7. The method according to claim 1, wherein spectral analysis of Raman scattered radiation occurs by sequential focusing of excitation radiation in the form of several linear excitation zones [i . . . i+n] within the measurement zone on the biological sample.

8. The method according to claim 7, wherein location-resolved spectral analysis of the Raman scattered radiation occurs by position-resolved spectral analysis by a two-dimensional CCD array detector, in which a linear excitation zone i in the first dimension of the CCD array is imaged true to position along its longitudinal extent and the spectral distribution of Raman scattered radiation in the second dimension of the CCD array is imaged from each point along the longitudinal extent of this excitation zone and local Raman spectra are recorded position-resolved.

9. The method according to claim 8, wherein the first family of local Raman spectra in the first excitation zone i is recorded in a first measurement cycle,
wherein in a second subsequent measurement cycle a second family of local Raman spectra on a second excitation zone i+1 adjacent to the first excitation zone i is recorded by moving the linear focus of the excitation radiation between measurement cycles from a first position relative to the biological sample fixed in the measurement one to a second position, and
wherein additional measurement cycles for additional locally adjacent excitation zones i +n are repeated, in which the families of local Raman spectra of all excitation zones [i . . . i+n] are combined to an overall image of position-resolved spectral distribution patterns of the biological sample fixed in the measurement zone (line scan).

10. The method according to claim 1, further comprising characterization of the biological sample or particles analyzed in the measured zone by determination of typical characteristics from the at least one Raman spectrum and comparison of the determined typical spectrum characteristics with stored spectrum characteristics.

11. The method according to claim 1, further comprising characterization of the biological sample or particle analyzed in the measurement zone by determination of typical characteristics from the photomicrograph image data and comparison of the determined image characteristics with stored image characteristics.

12. The method according to claim 10, wherein from comparison of the determined characteristics according to established criteria, characterization of the biological sample or particles contained in the biological sample occurs on parameters chosen from: genus, species, degree of differentiation, vitality and chemical composition.

13. The method according to claim 1, wherein the particles from the biological fluid are fixed on the "top" of the perforated plate by optionally temporary application of a dynamic and/or static pressure gradient in the direction of the opposite "bottom" of the perforated plate.

14. The method according to claim 1, wherein an individual particle is precisely fixed in an individual perforation of the perforated plate.

15. The method according to claim 1, further comprising preselection of the particles to be analyzed by separating the particles according to size on several perforated plates connected one behind the other in the fluid cell in the direction of flow with different perforation diameters.

16. The method according to claim 1, further comprising detection of any contamination in the biological fluid using the determined spectrum and/or image characteristics, in which the presence of infectious particles in the biological fluid is demonstrated with sufficient agreement of the characteristics and the absence of contamination of the biological fluid is demonstrated with a lack of agreement of the characteristics.

17. The method according to claim 1, wherein excitation radiation in the excitation zone has a wavelength of 785±60 nm or 250±50 nm.

18. The method according to claim 1, wherein the at least one perforated plate includes a top side and a bottom side and the method further comprises applying a partial vacuum to the bottom side of the perforated plate so as to at least temporarily fix the particles on the top side of the at least one perforated plate at the one or more perforations.

19. A device for optical-spectroscopic analysis of biological samples, comprising:
a sample holder unit for stationary fixation of the biological sample in a measurement zone;
excitation radiation unit appropriate for excitation of Raman scattered radiation by means of excitation radiation in an excitation zone within the measurement zone; and
analysis unit appropriate for spectral analysis of Raman scattered radiation emitted in the excitation zone of the biological sample;
wherein the biological sample is a biological fluid and the sample holder unit is a fluid cell traversable by the biological fluid in which the fluid cell has means that are suitable for retaining and reversible temporary fixation of any particles contained in the biological fluid in a measurement zone of the fluid cell
wherein the fluid cell has at least one first perforated plate with one or more perforations with a first diameter configured to retain the particles in the fluid cell; and
wherein the several perforations of the perforated plate are arranged in a regular structure.

20. The device according to claim 19, wherein the first diameter is 1µm or less.

21. The device according to claim 19, wherein the fluid cell has a second perforated plate with one or more perforations with a second diameter in which the second perforated plate is arranged upstream of the first perforated plate in the flow direction of the biological fluid through the fluid cell and in which the second diameter is greater than the first diameter.

22. The device according to claim 21, wherein the second diameter is from 2 to 6 µm.

23. The device according to claim 19, wherein the fluid cell has at least one microfluidic flow channel configured to retain the particles of the fluid cell.

24. The device according to claim 19, wherein the fluid cell has radiation-transparent material at least in the area of the excitation zone chosen from: silicate glass, quartz glass, silicon, silicon dioxide, silicon nitride, calcium fluoride glass, barium fluoride glass, zinc selenide glass, zinc sulfide glass and germanium glass.

25. The device according to claim 19, further comprising a line focusing unit for focusing of the excitation radiation of the excitation radiation unit on particles retained in the fluid cell in the form of a linear excitation zone.

26. The device according to claim 25, wherein the line focusing unit also has a scanner unit suitable for moving the linear excitation zone across its longitudinal extent over the retained particles.

27. The device according to claim 19, further comprising a microscope unit suitable for photomicrographic imaging analysis of the retained particles, in which the optical image of the retained particles is imaged on an image recording system.

28. The device according to claim 27, wherein the microscope unit is a phase contrast/fluorescence transmission microscope.

29. The device according to claim 19, wherein the analysis unit contains:
- a two-dimensional CCD array suitable for position-resolved electrical detection of Raman scattered radiation;
- an optical grating suitable for spectral separation of Raman scattered radiation emitted in the excitation zone of the biological sample; and
- an optical arrangement suitable for position-resolved imaging of spectrally separated Raman scattered radiation from the excitation zone on the CCD array so that in the first dimension the excitation zone is imaged true to position along its longitudinal extent and in the second dimension the spectral distribution of each point is imaged along the longitudinal extent of the excitation zone.

30. The device according to claim 19, wherein the analysis unit is designed as a lens-based Raman spectrograph.

31. The device according to claim 19, wherein the analysis unit has an optimized detection sensitivity for Raman scattered radiation in the range from 200 to 3500 $cm^{-1}$.

32. The device according to claim 19, further comprising:
- a computer device suitable for determination of characteristics of the Raman spectrum recorded by the analysis unit for comparison of the determined characteristics with stored characteristics and to determine the results of the comparison of the characteristics;
- a memory element suitable for storage of the stored characteristics, the determined characteristics and the result of the characteristic comparison of the computer; and
- a display element suitable for displaying the results of the characteristic comparison.

33. The device according to claim 19, wherein the device is configured to be for noninvasive, nondestructive checking of biological fluids for sterility and contamination.

34. The device according to claim 19, wherein the device is configured to be used for noninvasive, nondestructive characterization of typing and/or selection of a biological cell contained in a fluid.

35. The device according to claim 19, the device being configured to be used for noninvasive, nondestructive characterization of the differentiation status of the biological cell contained in a fluid.

36. The device according to claim 19, the device being configured to be used for noninvasive, nondestructive characterization or typing of tissues or tissue parts.

37. The device according to claim 19, the device being configured to be used for noninvasive, nondestructive characterization or typing of allogenic or autologous implants.

38. A device for optical-spectroscopic analysis of biological samples, comprising:
- a sample holder unit for stationary fixation of the biological sample in a measurement zone;
- excitation radiation unit appropriate for excitation of Raman scattered radiation by means of excitation radiation in an excitation zone within the measurement zone; and
- analysis unit appropriate for spectral analysis of Raman scattered radiation emitted in the excitation zone of the biological sample;
- wherein the biological sample is a biological fluid and the sample holder unit is a fluid cell traversable by the biological fluid in which the fluid cell has at least one perforation array suitable for retaining and reversible temporary fixation of particles contained in the biological fluid in a measurement zone of the fluid cell.

39. The device according to claim 38, wherein the device is integrated into a production chain such that spectral analysis of Raman scattered radiation occurs at least quasicontinuosuly without having to remove samples from the production chain to analyze them separately.

* * * * *